(12) United States Patent
Slank

(10) Patent No.: US 11,484,542 B2
(45) Date of Patent: Nov. 1, 2022

(54) SPECIALIZED TONGUE SPRAY CONTAINING GYMNEMIC ACID AND EXOGENOUS KETONES

(71) Applicant: Adam Slank, Austin, TX (US)

(72) Inventor: Adam Slank, Austin, TX (US)

(*) Notice: Subject to any disclaimer, the term of this patent is extended or adjusted under 35 U.S.C. 154(b) by 0 days.

(21) Appl. No.: 16/427,166

(22) Filed: May 30, 2019

(65) Prior Publication Data

US 2019/0365789 A1   Dec. 5, 2019

Related U.S. Application Data

(60) Provisional application No. 62/678,102, filed on May 30, 2018.

(51) Int. Cl.
| | | |
|---|---|---|
| A61K 8/42 | (2006.01) |
| A61K 31/164 | (2006.01) |
| A61K 31/165 | (2006.01) |
| A61K 31/404 | (2006.01) |
| A61K 31/4164 | (2006.01) |
| A61K 9/70 | (2006.01) |
| A61K 8/49 | (2006.01) |
| A61K 9/06 | (2006.01) |
| A61Q 19/00 | (2006.01) |
| A61K 8/02 | (2006.01) |
| A61P 17/00 | (2006.01) |
| A61K 8/44 | (2006.01) |
| A61Q 19/08 | (2006.01) |
| A61K 31/704 | (2006.01) |
| A61K 9/00 | (2006.01) |
| A61K 31/12 | (2006.01) |

(52) U.S. Cl.
CPC .......... *A61K 31/704* (2013.01); *A61K 9/006* (2013.01); *A61K 9/0056* (2013.01); *A61K 31/12* (2013.01)

(58) Field of Classification Search
None
See application file for complete search history.

(56) References Cited

U.S. PATENT DOCUMENTS

| | | |
|---|---|---|
| 9,421,217 B2 | 8/2016 | Goldstein et al. |
| 9,585,905 B2 | 3/2017 | Goldstein et al. |
| 9,675,577 B2 | 6/2017 | D'Agostino |
| 2006/0110415 A1* | 5/2006 | Gupta .................. A61K 8/0212 424/59 |

* cited by examiner

*Primary Examiner* — Layla Soroush
(74) *Attorney, Agent, or Firm* — Select Patents; Ashkon Cyrus

(57) ABSTRACT

The present disclosure relates to a tongue spray containing gymnemic acid together with a form of exogenous ketones. The present disclosure also relates to methods of reducing or eliminating sugar consumption and reducing sugar withdrawal symptoms via administration of such composition to a subject.

5 Claims, No Drawings

SPECIALIZED TONGUE SPRAY CONTAINING GYMNEMIC ACID AND EXOGENOUS KETONES

CROSS REFERENCE TO RELATED APPLICATIONS

This application claims the benefit of provisional patent application 62/678,102, filed May 30, 2018, the entirety of which is incorporated by reference.

FIELD OF THE INVENTION

The present disclosure relates to a tongue spray containing gymnemic acid together with a form of exogenous ketones. The present disclosure also relates to methods of reducing or eliminating sugar consumption and reducing sugar withdrawal symptoms via administration of such composition to a subject.

BACKGROUND OF THE INVENTION

Many users wish to eliminate sugar from their diet. Gymnemic acid is known to temporarily block the sensation of sweet taste when applied directly to the oral cavity. U.S. Pat. Nos. 9,585,902 and 9,421,217 describe various sweet taste receptor antagonist compositions containing gymnemic acid. However, eliminating sugar from the diet can cause adverse symptoms and withdrawal symptoms as the body converts from burning glucose to burning ketones. Thus, the methods described in these references fail to alleviate the adverse symptoms of sugar withdrawal.

Traditionally, a person using gymnemic acid to wean themselves completely off of sugar would have to suffer for up to six days during this conversion process. In the field of nutrition, one would prescribe extra hydration as the only means to deal with the symptoms. Other methods would be applied in an attempt to minimize the symptoms of headaches, brain fog, lethargy, irritability, and body aches. Moreover, the severity of the symptoms would cause users to abandon the restrictive diet prematurely and return to sugar consumption in order to lessen the discomfort.

However, these traditional remedies do not work to address the real problem causing the symptoms, which is the shift in the body's fuel supply from glucose to ketones. Thus, what is needed is a method to deliver gymnemic acid directly to the user whilst mitigating the withdrawal symptoms of sugar. This disclosure addresses this need. U.S. Pat. No. 9,675,577 describes various types of exogenous ketones. The present disclosure relates to a tongue spray containing gymnemic acid together with a form of exogenous ketones.

SUMMARY OF THE INVENTION

The present disclosure relates to a tongue spray containing gymnemic acid together with a form of exogenous ketones. This provides compositions to directly contact the oral cavity to block sweet taste receptors located therein, while also preventing sugar withdrawal symptoms by providing through the exogenous ketones an alternative energy source during the initial withdrawal symptoms accompanying sugar abstinence.

As the sweet taste blocking effect of gymnemic acid eliminates the incentive for sugar consumption, there is a need for an effective means to reduce the severity and length of withdrawal symptoms since the time sugar is removed from the diet. This need is met by the exogenous ketones provided in the systems and methods of the present disclosure, which preferably allow for delivery of gymnemic acid to the oral cavity together with a form of ketone, mitigating or preventing the uncomfortable natural response of the body to entering a sugar free ketogenic state. This results in less symptoms for a user during the transition away from sugar, fructose, and glucose in the diet.

In general and according to certain embodiments, the lingual delivery forms and compositions of the present disclosure delivering gymnemic acid, together with a form of exogenous ketone, directly to the sweet taste receptors of the tongue, resulting in exceptional durations of sweetness blockade while simultaneously reducing or eliminating the sugar withdrawal symptoms.

The present disclosure may be directed to a lingual delivery form comprising gymnemic acid and at least one form of ketone. The lingual delivery may include, but is not limited to, a lozenge, an orally disintegrating tablet, an orally dispersible tablet, a troche, a hard candy, a soft candy, a jelly, a gum, an edible film, an orally dissolvable film, a wafer, a drop, an oral spray, a liquid, a powder and combinations thereof.

The form of ketone may include, but is not limited to, BHB, Beta-Hydroxybutyrate, in the form of ester and in the form of salts where the BHB is bound to calcium, sodium, and magnesium, and combinations thereof. The form of ketone may be a GRAS (Generally Recognized as Safe) approved ketone salt, such as beta-hydroxybutyrate or beta-hydroxybutyric acid.

The gymnemic acid may be present as an inorganic salt of gymnemic acid, an organic salt of gymnemic acid, a cyclodextrin complex of gymnemic acid, a cryptand complex of gymnemic acid, a hydrate of gymnemic acid, a solvate of gymnemic acid, and combinations thereof. The solvate of gymnemic acid may include ethanol solvates of gymnemic acid.

The lingual delivery form may further comprise mint.

The bitter taste inhibitor may include, but is not limited to, sodium salt, a lipoprotein, and combinations thereof.

The lingual delivery form may further comprise at least one sour taste inhibitor. The sour taste inhibitor may be miraculin.

Although specific advantages have been enumerated above, various embodiments may include some, none, or all of the enumerated advantages. Additionally, other technical advantages may become readily apparent to one of ordinary skill in the art after review of the following figures and description.

DETAILED DESCRIPTION OF THE INVENTION

It should be understood at the outset that, the present disclosure should in no way be explicitly limited to the exemplary implementations and techniques illustrated in the drawings and described below. All publications, patent applications, patents, figures and other references mentioned herein are expressly incorporated by reference in their entirety.

As defined in the present disclosure, the phrase "sweetness blockade" is defined as the reduction of the perceptible sweetness of a food or beverage or other substance introduced into the mouth.

As defined in the present disclosure, the phrase "exogenous ketone" is defined as any ketone not produced within the body.

The lingual delivery forms and the compositions of the present disclosure comprise gymnemic acid and exogenous ketones. As defined in the present disclosure, gymnemic acid refers to extracts of the plant Gymnema sylvestre which contain one or more triterpenoid saponins capable of inhibiting the sensation of sweet taste in a human, as well as compositions comprising gymnemic acid that include the synthetic counterparts of these extracted triterpenoid saponins.

Gymnemic acid provides a sweetness blockade, wherein any sweet food or drink or other introduced to the mouth following delivery of gymnemic acid to the oral cavity do not taste as sweet or their sweet flavor is diminished. It is known that use of gymnemic acid through delivery to the oral cavity, including the tongue, stops cravings for sweet tastes in food or drink, results in a decreased consumption of such high-calorie foods. However, a drawback to using gymnemic acid in this known manner is that the instant removal of sugar from the diet can have unpleasant withdrawal symptoms. Thus, there exists a continuing need for improved gymnemic acid-based compositions that can block the sensation of sweet taste while reducing or eliminating the symptoms of sugar withdrawal.

It has been beneficially found that when gymnemic acid is combined with ketones, sugar withdrawal symptoms are greatly minimized or completely eliminated. Moreover, it has been beneficially found that compositions of gymnemic acid together with a form of ketone can provide increased comfort, energy and alertness compared to gymnemic acid alone.

The present disclosure provides delivery of gymnemic acid to the oral cavity in order to block the sensation of sweetness in combination with exogenous ketones to reduce sugar withdrawal symptoms. Thus, during the ingestion of any sweet food or drink, the sweetness does not lead to the perception of sweet taste, and the exogenous ketones to alleviate any sugar withdrawal symptoms.

In general and according to certain embodiments, the lingual delivery forms and compositions of the present disclosure deliver gymnemic acid to the sweet taste receptors of the tongue in combination with exogenous ketones, resulting in sweetness blockade while simultaneously reducing or eliminating sugar withdrawal.

The unique and surprising performance of compositions containing both gymnemic acid and a form of ketone provides an advantage over prior art gymnemic acid formulations, providing more comfortable periods of sweet taste blocking and allowing a subject to maintain the elimination of sugar from the diet without experiencing severe sugar withdrawal symptoms.

It can be appreciated that application of a composition comprising gymnemic acid together with a form of ketone form a synergistic effect, as the gymnemic acid proves a sweetness block and the ketones provide a reduction in sugar withdrawal which ultimately leads to less consumption of such foods.

One embodiment of the present disclosure comprises a lingual delivery form comprising gymnemic acid and a form of ketone. Examples of such lingual delivery forms include oral sprays, tablets, orally disintegrating tablets, liquids, and powders. In one embodiment, a user maintains a solid lingual delivery form comprising gymnemic acid and a form of ketone in the oral cavity for about 1 to 5 minutes. In another embodiment, a user maintains a liquid lingual delivery form comprising gymnemic acid and a form of ketone in the oral cavity for about 1 to 5 minutes.

Yet another aspect of the present disclosure is a composition comprising gymnemic acid and a form of ketone together with at least one sour taste inhibitor.

The gymnemic acid used in the lingual delivery forms and compositions of the present disclosure can be of any purity known in the art to be effective in blocking sweetness.

The gymnemic acid used in the lingual delivery forms and compositions of the present disclosure can be in various forms known in the art such as an inorganic salt, an ammonium salt, an amino salt including a polyamino salt, an organic salt, a cyclodextrin complex, a cryptand complex, a hydrate, or a solvate of gymnemic acid, or any combination thereof. Examples of inorganic salts of gymnemic acid known in the art include, but are not limited to, alkali metal salts, such sodium and potassium, alkaline earth metal salts, such as magnesium and calcium, transition metal salts, such as manganese, iron, and zinc, and rare earth metal salts, such as lanthanum, europium and terbium. Examples of ammonium salts of gymnemic acid known in the art include, but are not limited to, ammonium salts, mono-alkyl-substituted ammonium salts such as a methylammonium salt, di-alkyl-substituted ammonium salts, such as a dimethylammonium salt, tri-alkyl-substituted ammonium salt, such as a trimethylammonium salt, or tetra-alkyl-substituted ammonium salts, such as a tetramethylammonium salt. Examples of polyamino salts of gymnemic acid known in the art include, but are not limited to, are di-amino salts, such as an ethylenediamine salt, tri-amino salts, such as an diethylenetriamine salt, tetra-amino salts, such as a triethylenetetramine salt, and other poly-amino salts, such as an .alpha.-polyornithine salt, an .alpha.-polylysine salt, a .gamma.-polyornithine salt, an .epsilon.-polylysine salt, or a chitosan salt. Examples of cyclodextrin complexes of gymnemic acid known in the art include, but are not limited to, .alpha.-cyclodextrin, .beta.-cyclodextrin, and .gamma.-cyclodextrin complexes of gymnemic acid. Examples of solvates of gymnemic acid known in the art include ethanol solvates of gymnemic acid and ethyl acetate solvates of gymnemic acid.

The gymnemic acid is present in any amount effective to partially or completely block the sensation of sweet taste in a subject for a period of time. Examples of such amounts known in the art include, but are not limited to, those in the range of about 0.01% to about 25% by weight, about 0.01% to about 10% by weight, about 0.01% to about 4% by weight, about 0.05% to about 2% by weight, about 0.01% to about 1% by weight, about 0.01% to about 0.5% by weight, and about 0.01% to about 0.2% by weight of the total weight of the lingual delivery form or composition. In certain embodiments, the gymnemic acid can be present in about 0.1% to 5% weight, 0.01 to 1% weight, about 0.01% to 0.5% weight, or about 0.01% to 0.2% weight of the lingual delivery form. In terms of absolute amount, the lingual delivery forms and compositions of the present invention may comprise about 0.1 mg to 200 mg of gymnemic acid, including but not limited to 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mg of gymnemic acid. The remaining portion of the lingual delivery form comprises exogenous ketones. Furthermore, the lingual delivery form can include flavors such as peppermint, spearmint, cinnamon, and menthol.

The lingual delivery form may further comprise mint. While the addition of mint to gymnemic acid cannot block any bitter taste, to the extent there is any remaining bitterness upon administration of the lingual delivery form comprising gymnemic acid and a form of ketone, the mint will mask or block it while the ketones provide energy to the user.

In certain embodiments, the compositions of the present invention comprise gymnemic acid, a form of ketone, and at least one sour taste inhibitor. Any sour taste inhibitor known in the art may be used. An example of such a sour taste inhibitor includes, but is not limited to, miraculin.

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure.

The invention claimed is:

1. An oral composition comprising:
about 0.1 mg to about 10 mg of gymnemic acid,
about 1 mg to about 10 mg of beta hydroxybutyrate ester, and mint,
wherein the gymnemic acid and hydroxybutyrate ester in the composition have a ratio by weight of less than 1:1 to suppress a sensation of sweetness, and wherein the exogenous ketone is present in an amount sufficient to reduce sugar withdrawal symptoms.

2. The oral composition of claim 1, wherein the composition is an orally disintegrating tablet.

3. The oral composition of claim 1, wherein the composition is a mouth spray.

4. The oral composition of claim 1, wherein the gymnemic acid is present in the range of from about 1 mg to about 5 mg.

5. The oral composition of claim 1, wherein the gymnemic acid is present in the range of from about 2 mg to about 10 mg.

* * * * *